US008715258B2

(12) United States Patent
Munakata et al.

(10) Patent No.: US 8,715,258 B2
(45) Date of Patent: *May 6, 2014

(54) ABSORBENT ARTICLE HAVING OUTWARDLY CONVEX LONGITUDINAL CENTRAL CHANNELS FOR IMPROVED PROTECTION

(75) Inventors: Yoko Munakata, Kobe (JP); Kiyoe Ohba, Ibaraki (JP)

(73) Assignee: The Procter and Gamble Company, Cincinnati, OH (US)

( * ) Notice: Subject to any disclaimer, the term of this patent is extended or adjusted under 35 U.S.C. 154(b) by 1442 days.

This patent is subject to a terminal disclaimer.

(21) Appl. No.: 11/289,844

(22) Filed: Nov. 30, 2005

(65) Prior Publication Data

US 2006/0116653 A1    Jun. 1, 2006

Related U.S. Application Data

(60) Provisional application No. 60/631,759, filed on Nov. 30, 2004.

(51) Int. Cl.
*A61F 13/536* (2006.01)
*A61F 13/537* (2006.01)

(52) U.S. Cl.
USPC ............ 604/385.101; 604/385.31; 604/380

(58) Field of Classification Search
USPC ............ 604/378–80, 385.01, 385.03–385.04, 604/385.101, 385.17, 387
See application file for complete search history.

(56) References Cited

U.S. PATENT DOCUMENTS

| 4,285,343 | A | * | 8/1981 | McNair .................. 604/387 |
| 4,425,130 | A | | 1/1984 | DesMarais |
| 4,589,876 | A | | 5/1986 | Van Tilburg |
| 4,687,478 | A | | 8/1987 | Van Tilburg |

(Continued)

FOREIGN PATENT DOCUMENTS

| DE | 29 703 589 U 1 | 7/1997 |
| EP | 1 016 393 A1 | 7/2000 |

(Continued)

OTHER PUBLICATIONS

Translation of JP 2003-052743.*

(Continued)

*Primary Examiner* — Melanie Hand
*Assistant Examiner* — Paula Craig
(74) *Attorney, Agent, or Firm* — Megan C. Hymore; Amanda T. Barry; Gary J. Foose

(57) ABSTRACT

An absorbent article having a pair of longitudinal edges, front and rear transverse edges, a front end region, a rear end region, and a central region disposed between the front and rear end regions. The absorbent article has a liquid pervious topsheet, a liquid impervious backsheet, an absorbent core disposed between the topsheet and the backsheet, and a pair of outwardly convex longitudinal central channels formed at least in the central region. The traversal distance of the pair of outwardly convex longitudinal central channels decreases towards both ends of the channels to define a central closed area. The absorbent article has a rear channel defining a rear closed area in the rear end region. The absorbent core is profiled within the central closed area so that the central region has a caliper that is greater than the caliper of the outside of the central closed area.

11 Claims, 4 Drawing Sheets

(56) References Cited

U.S. PATENT DOCUMENTS

| | | | |
|---|---|---|---|
| 4,781,710 A * | 11/1988 | Megison et al. | 604/378 |
| 4,865,597 A * | 9/1989 | Mason et al. | 604/385.31 |
| 4,950,264 A | 8/1990 | Osborn, III | |
| 5,009,653 A | 4/1991 | Osborn, III | |
| 5,171,302 A * | 12/1992 | Buell | 604/385.23 |
| 5,176,672 A * | 1/1993 | Bruemmer et al. | 604/385.19 |
| 5,197,959 A * | 3/1993 | Buell | 604/385.23 |
| 5,234,422 A | 8/1993 | Sneller et al. | |
| 5,267,992 A | 12/1993 | Van Tilburg | |
| 5,312,386 A | 5/1994 | Correa et al. | |
| 5,342,337 A * | 8/1994 | Runeman et al. | 604/378 |
| 5,374,260 A | 12/1994 | Lemay et al. | |
| 5,389,094 A | 2/1995 | Lavash et al. | |
| 5,439,458 A | 8/1995 | Noel et al. | |
| 5,453,013 A | 9/1995 | Billings et al. | |
| 5,460,623 A | 10/1995 | Emenaker et al. | |
| 5,464,402 A * | 11/1995 | Zajaczkowski | 604/385.21 |
| 5,466,232 A | 11/1995 | Cadieux et al. | |
| 5,558,663 A | 9/1996 | Weinberger et al. | |
| 5,569,231 A | 10/1996 | Emenaker et al. | |
| 5,591,148 A * | 1/1997 | McFall et al. | 604/378 |
| 5,591,150 A * | 1/1997 | Olsen et al. | 604/385.23 |
| 5,613,961 A * | 3/1997 | DiPalma et al. | 604/369 |
| 5,624,423 A * | 4/1997 | Anjur et al. | 604/385.21 |
| H1698 H | 11/1997 | Lloyd et al. | |
| 5,746,729 A | 5/1998 | Wada et al. | |
| 5,795,345 A | 8/1998 | Mizutani et al. | |
| 5,797,894 A | 8/1998 | Cadieux et al. | |
| 5,830,296 A | 11/1998 | Emenaker et al. | |
| 5,855,572 A * | 1/1999 | Schmidt | 604/378 |
| 5,954,705 A * | 9/1999 | Sawaki et al. | 604/385.101 |
| 6,074,376 A | 6/2000 | Mills | |
| 6,152,904 A * | 11/2000 | Matthews et al. | 604/378 |
| 6,159,190 A * | 12/2000 | Tanaka et al. | 604/385.24 |
| 6,217,563 B1 * | 4/2001 | Van Gompel et al. | 604/385.101 |
| 6,300,538 B1 * | 10/2001 | Lindquist et al. | 604/369 |
| 6,326,525 B1 | 12/2001 | Hamajima et al. | |
| 6,348,047 B1 * | 2/2002 | Harper | 604/385.17 |
| 6,371,948 B1 * | 4/2002 | Mizutani | 604/385.01 |
| 6,394,989 B2 | 5/2002 | Mizutani | |
| 6,395,956 B1 * | 5/2002 | Glasgow et al. | 604/378 |
| 6,425,889 B1 * | 7/2002 | Kitaoka et al. | 604/385.01 |
| 6,425,890 B1 * | 7/2002 | Samuelsson et al. | 604/385.17 |
| 6,492,574 B1 * | 12/2002 | Bednarz et al. | 604/378 |
| 6,503,233 B1 * | 1/2003 | Chen et al. | 604/385.01 |
| 6,506,961 B1 * | 1/2003 | Levy | 604/380 |
| 6,515,195 B1 * | 2/2003 | Lariviere et al. | 604/380 |
| 6,517,525 B1 * | 2/2003 | Berthou et al. | 604/385.101 |
| 6,563,013 B1 | 5/2003 | Murota | |
| 6,613,955 B1 * | 9/2003 | Lindsay et al. | 604/378 |
| 6,617,490 B1 | 9/2003 | Chen et al. | |
| 6,667,424 B1 | 12/2003 | Hamilton et al. | |
| 6,673,982 B1 * | 1/2004 | Chen et al. | 604/378 |
| 6,692,603 B1 * | 2/2004 | Lindsay et al. | 156/209 |
| 6,740,069 B2 | 5/2004 | Drevik | |
| 6,824,534 B2 * | 11/2004 | Mishima et al. | 604/385.01 |
| 6,858,771 B2 * | 2/2005 | Yoshimasa et al. | 604/380 |
| 6,965,058 B1 * | 11/2005 | Raidel et al. | 604/367 |
| 6,986,761 B1 | 1/2006 | Hines et al. | |
| 7,056,311 B2 * | 6/2006 | Kinoshita et al. | 604/385.04 |
| 7,078,583 B2 | 7/2006 | Kudo et al. | |
| 7,122,023 B1 * | 10/2006 | Hinoki | 604/385.101 |
| 7,279,613 B2 * | 10/2007 | Nozaki et al. | 604/380 |
| 7,312,372 B2 | 12/2007 | Miyama et al. | |
| 7,368,627 B1 * | 5/2008 | Widlund | 604/378 |
| 7,754,940 B2 * | 7/2010 | Brisebois et al. | 604/380 |
| 2001/0039406 A1 * | 11/2001 | Hamajima et al. | 604/367 |
| 2002/0013567 A1 * | 1/2002 | Mishima et al. | 604/385.101 |
| 2002/0052587 A1 * | 5/2002 | Magnusson et al. | 604/378 |
| 2002/0052589 A1 * | 5/2002 | Strand | 604/385.01 |
| 2002/0065497 A1 * | 5/2002 | Kolby-Falk | 604/368 |
| 2002/0087133 A1 * | 7/2002 | Osterdahl et al. | 604/374 |
| 2002/0156450 A1 * | 10/2002 | Drevik et al. | 604/385.101 |
| 2003/0050617 A1 * | 3/2003 | Chen et al. | 604/378 |
| 2003/0088222 A1 * | 5/2003 | Yoshimasa et al. | 604/380 |
| 2003/0120235 A1 * | 6/2003 | Boulanger | 604/378 |
| 2003/0125700 A1 | 7/2003 | Drevik | |
| 2003/0135177 A1 * | 7/2003 | Baker | 604/368 |
| 2004/0176734 A1 * | 9/2004 | Rasmussen et al. | 604/380 |
| 2004/0260262 A1 * | 12/2004 | Nishitani et al. | 604/385.04 |
| 2004/0267220 A1 * | 12/2004 | Hull et al. | 604/380 |
| 2005/0182374 A1 * | 8/2005 | Zander et al. | 604/380 |
| 2005/0256472 A1 * | 11/2005 | Tsutsui | 604/378 |
| 2006/0116652 A1 | 6/2006 | Miura et al. | |

FOREIGN PATENT DOCUMENTS

| | | |
|---|---|---|
| EP | 1208824 A2 * | 5/2002 |
| EP | 1 269 950 A | 1/2003 |
| JP | 2000-051269 | 2/2000 |
| JP | 2001-095842 | 4/2001 |
| JP | 2001-314445 | 11/2001 |
| JP | 2002-253612 | 9/2002 |
| JP | 2002-345888 | 12/2002 |
| JP | 2003-052743 | 5/2003 |
| JP | 2003-180733 | 7/2003 |
| WO | WO 95/15139 | 6/1995 |
| WO | WO 02/41817 A | 5/2002 |

OTHER PUBLICATIONS

Definition of "envelope", Webster's Third New International Dictionary, Unabridged.*
U.S. Appl. No. 11/289,812, filed Nov. 30, 2005, Miura et al.
PCT International Search Report Dated Apr. 4, 2006.
Office Action for U.S. Appl. No. 11/289,812 dated Jun. 3, 2008; Tsunetoshi et al.; filed Nov. 30, 2005.
Office Action for U.S. Appl. No. 11/289,812 dated Jun. 16, 2009; Tsunetoshi et al.; filed Nov. 30, 2005.
Office Action for U.S. Appl. No. 11/289,812 dated Aug. 19, 2009; Tsunetoshi et al.; filed Nov. 30, 2005.
Office Action, mailed Feb. 25, 2010, U.S. Appl. No. 11/289,812, filed Nov. 30, 2005, Inventors: Tsuneotoshi Miura, et al.

* cited by examiner

ABSORBENT ARTICLE HAVING OUTWARDLY CONVEX LONGITUDINAL CENTRAL CHANNELS FOR IMPROVED PROTECTION

CROSS REFERENCE TO RELATED APPLICATION

This application claims the benefit of U.S. Provisional Application No. 60/631,759, filed on Nov. 30, 2004.

FIELD OF THE INVENTION

The present invention relates to absorbent articles such as sanitary napkins, pantiliners, and incontinence pads. More particularly, the present invention relates to a sanitary napkin having a pair of outwardly convex longitudinal central channels.

BACKGROUND OF THE INVENTION

Absorbent articles, such as sanitary napkins, pantiliners, and incontinence pads, are typically worn in the crotch region of an undergarment. These devices are designed to absorb and retain liquids and other discharges from the human body to prevent body and garment soiling. The aforementioned types of absorbent articles are typically placed in a garment such as the wearer's panty and worn between the wearer's legs, adjacent to the genital (or fluids discharge source) area of the body.

Conventional relatively thick, overnight, or extra protection sanitary napkin products currently marketed in Japan provide some protection from soiling by utilizing a combination of increased product length and thickness (which may include a profiled or varied caliper). These products, however, are not believed to conform or fit to the body of the wearer as closely as possible, particularly at the portions that are adjacent to the discharge portion of body fluids in use. Thus, leakage is possible, particularly at both the central region, the rear region and/or the side edges of these products. This issue is seen not only in conventional relatively thick, overnight, or extra protection sanitary napkin products but also other conventional relatively thinner and smaller sanitary napkin products in the market.

Thus, there is a need for an absorbent article that provides improved protection from soiling. There is another need for a sanitary napkin that fits closer to the wearer's body in the areas where menses and other body fluids originate.

SUMMARY OF THE INVENTION

In one aspect of the invention, the invention is directed to an absorbent article having a pair of longitudinal edges, front and rear transverse edges, a front end region, a rear end region, and a central region disposed between the front and rear end regions. The absorbent article comprises: a liquid pervious topsheet; a liquid impervious backsheet; an absorbent core disposed between the topsheet and the backsheet; a pair of outwardly convex longitudinal central channels formed at least in the central region. The traversal distance of the pair of outwardly convex longitudinal central channels decreases towards the both ends of the channels to define a central closed area which has a maximum length of 80-220 mm and a maximum width of 25-70 mm. The absorbent article further comprises a rear channel defining a rear closed area in the rear end region. Preferably, the absorbent core is profiled within the central closed area so that the central region has a caliper that is greater than the caliper of the outside of the central closed area.

In another aspect of the invention, the absorbent article has a pair of longitudinal edges, front and rear transverse edges, a front end region, a rear end region, and a central region disposed between the front and rear end regions. The absorbent article comprises: a liquid pervious topsheet; a liquid impervious backsheet; an absorbent core disposed between the topsheet and the backsheet. The absorbent article further comprises a pair of longitudinal channels formed in the front end region, the central region and the rear end region; and a pair of central side flaps each extending laterally outward in the central region. The pair of longitudinal channels has (1) an outwardly convex channel portion in the central region, (2) a front inwardly concave channel portion at the transition area between the front end region and the central region, and (3) a rear inwardly concave channel portion at the transition area between the rear end region and the central region.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

Herein, "comprise" and "include" mean that other elements and/or other steps which do not affect the end result can be added. Each of these terms encompasses the terms "consisting of" and "consisting essentially of".

Herein, "absorbent article" refers to articles which absorb and contain body exudates or discharges such as body fluids, and is intended to include sanitary napkins, pantiliners, diapers, and incontinence pads (and other articles worn in the crotch region of a garment).

Herein, "disposable" refers to articles which are intended to be discarded after a single use, composted, or otherwise disposed of in an environmentally compatible manner. (That is, they are not intended to be laundered or otherwise restored or reused as an absorbent article.)

Herein, "sanitary napkin" refers to articles which are worn by females adjacent to the pudendal region which are intended to absorb and contain the various exudates which are discharged from the body (e.g., blood, menses, and urine). It should be understood, however, that the present invention is also applicable to other feminine hygiene or catamenial pads such as pantiliners, diapers, and incontinence pads (and other articles worn in the crotch region of a garment).

Herein, "joined" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element.

Herein, "body surface" refers to surfaces of absorbent articles and/or their component members which face the body of the wearer, while "garment surface" refers to the opposite surfaces of the absorbent articles and/or their component members that face away from the wearer when the absorbent articles are worn. Absorbent articles and components thereof, including the topsheet, backsheet, absorbent core, and any individual layers of their components, have a body surface and a garment surface.

Figure 1:
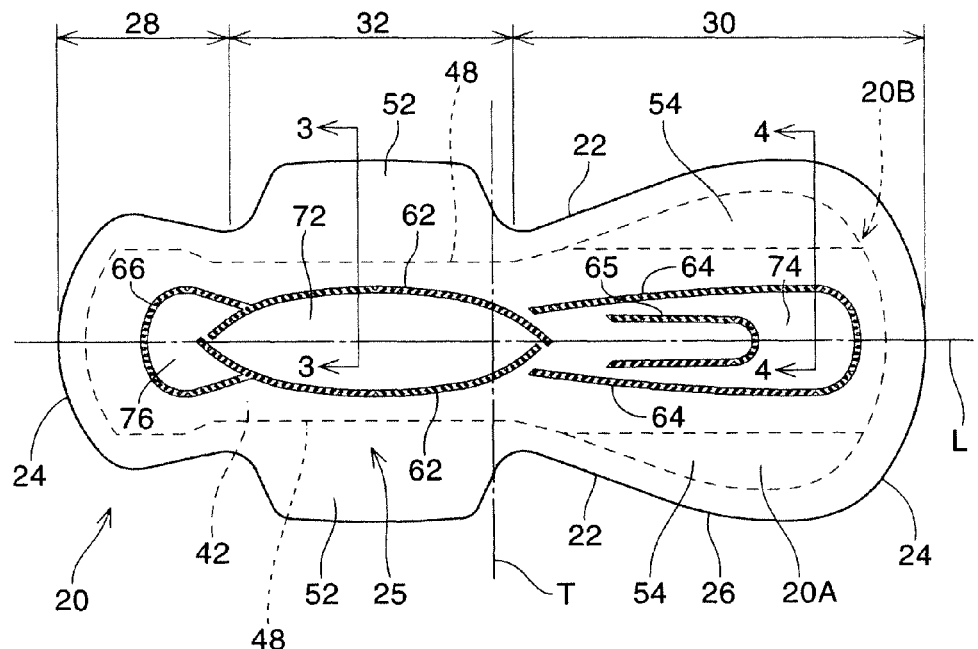
FIG. 1 is a top plane view of a preferred embodiment of the absorbent article of the present invention.

FIG. 1 is a top plane view of a preferred embodiment of the absorbent article of the present invention. In preferred embodiments shown in FIGS. 1-8, the absorbent article is a relatively thick, overnight, extra protection, disposable sanitary napkin 20.

Figure 2:
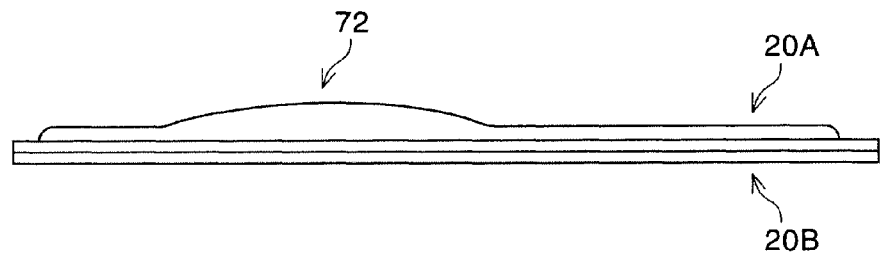
FIG. 2 is a side view of the absorbent article shown in FIG. 1.

The sanitary napkin 20 has two surfaces, a liquid pervious body-contacting surface or body surface 20A and a liquid impervious garment surface 20B. FIG. 2 is a side view of the sanitary napkin 20 shown in FIG. 1. The body surface 20A is intended to be worn adjacent to the body of the wearer. The garment surface 20B of the sanitary napkin 20 is on the opposite side and is intended to be placed adjacent to the wearer's undergarments when the sanitary napkin 20 is worn.

Referring to FIG. 1, the sanitary napkin 20 has two centerlines, a longitudinal centerline L and a transverse centerline T. Herein, "longitudinal" refers to a line, axis or direction in the plane of the sanitary napkin 20 that is generally aligned with (e.g., approximately parallel to) a vertical plane which bisects a standing wearer into left and right body halves when the sanitary napkin 20 is worn. Herein, "transverse" or "lateral" refers to a line, axis or direction which lies within the plane of the sanitary napkin 20 that is generally perpendicular to the longitudinal direction.

The sanitary napkin 20 has two spaced apart longitudinal edges 22 and two spaced apart transverse or end edges (or "ends") 24, which together form the periphery 26 of the sanitary napkin 20. The sanitary napkin 20 also has two end regions, i.e., a front end region 28 and a rear end region 30. A central region 32 is disposed between the end regions 28 and 30. The sanitary napkin 20 includes a pair of central side flaps 52 in the central region 32 and a pair of rear side flaps 54 in the rear end region 30. Each pair of central and rear side flaps 52 and 54 extends laterally outward from a main body portion 25 in the central region 32 and the rear end region 30, respectively.

The front end region 28 is defined as the area that is placed to the front of the wearer's body when the sanitary napkin 20 is worn. The rear end region 30 is defined as the area that is placed to the rear of the wearer's body. The central region 32 is defined as the area that is generally located directly below the perineum of the wearer and which receives the greatest amount of menses.

In a preferred embodiment, each region can be defined with respect to the positions of the side flaps 52 and 54. The front end region 28 ends at the transition area where the traversal distance between the two longitudinal edges 22 starts to increase towards the central region 32 as shown in FIG. 1. Similarly, the rear end region 30 ends at the transition area where the traversal distance between the two longitudinal edges 22 starts to increase towards the central region 32 as shown in FIG. 1.

In other words, each region can be defined with respect to the curve of the longitudinal edge 22. The front end region 28 ends at the transition area where the curve of the longitudinal edge 22 starts to extend laterally outward at a higher rate than before as shown in FIG. 1. Similarly, the rear end region 30 ends at the transition area where the curve of the longitudinal edge 22 starts to extend laterally outward at a higher rate than before as shown in FIG. 1.

Figure 3:
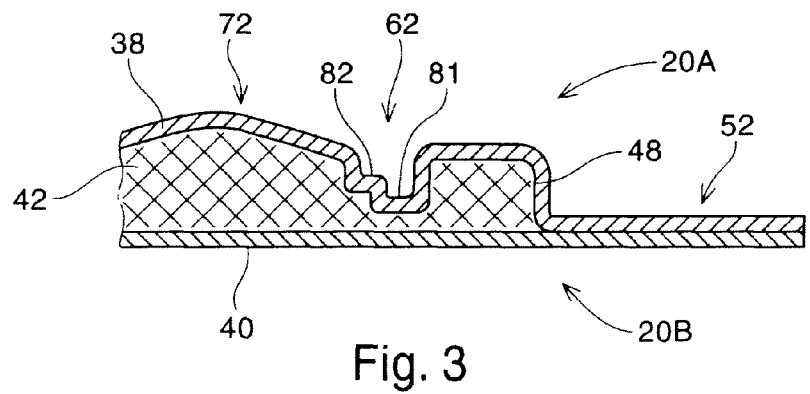
FIG. 3 is a schematic cross-sectional view of the absorbent article shown in FIG. 1 taken along line 3-3 of FIG. 1.

FIG. 3 is a cross-sectional view of the sanitary napkin 20 taken along the section line 3-3 in FIG. 1, which shows the individual components of the sanitary napkin 20 shown in FIG. 1. The sanitary napkin 20 shown in FIG. 3 generally comprises at least three primary components, i.e., a liquid pervious topsheet 38; a liquid impervious backsheet 40; an absorbent core 42 having longitudinal edges 48 disposed between the topsheet 38 and the backsheet 40. The central side flaps 52 extend laterally outward from the corresponding longitudinal edge 48 of the absorbent core 42 in the central region 32. The topsheet 38, backsheet 40, and absorbent core 42 can comprise any types of materials known in the art as being suitable for such components of an absorbent article or a sanitary napkin.

The topsheet 38 is preferably compliant, soft feeling, and non-irritating to the wearer's skin. Further, the topsheet 38 is liquid permeable or pervious, permitting body fluids (e.g., menses and/or urine) to readily penetrate through its thickness. A suitable liquid permeable material for the topsheet 38 may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet 38 includes a nonwoven web, the web may be manufactured by a wide number of known techniques. For example, the web may be spunbonded, carded, wet-laid, melt-blown, hydroentangled, combinations of the above, or the like.

A particularly suitable material for the topsheet 38 includes an apertured formed film. Apertured formed films are preferred for the topsheet 38 because they are pervious to body fluids and, if properly apertured, have a reduced tendency to allow liquids to pass back through and rewet the wearer's skin. Thus, the body surface of the formed film (i.e., the body surface 22 of the sanitary napkin 20) remains dry, thereby reducing body soiling and creating a more comfortable feel for the wearer. A preferred material for the topsheet 38 is a macroscopically expanded, three-dimensional formed polyethylene film. One preferred material for the topsheet 38 is available from Tredegar Film Products, Indiana, USA, under Code No. X-27121.

The backsheet 40 is impervious to body fluids and is preferably manufactured from a thin plastic film, although other flexible liquid impervious materials may also be used. Herein, "flexible" refers to materials which are compliant and will readily conform to the general shape and contours of the human body. The backsheet 40 prevents the body fluids absorbed and contained in the absorbent core 42 from wetting articles which contact the absorbent article such as bed sheets, pants, pajamas and undergarments. The backsheet 40 may thus include a woven or nonwoven material, polymeric films such as thermoplastic films of polyethylene or polypropylene, or composite materials such as a film-coated nonwoven material. The backsheet 40 can include a single layer material, or two or more layers of materials. The backsheet 40 preferably has a thickness of from about 0.012 mm (0.5 mil) to about 0.081 mm (3.4 mils). In a preferred embodiment, the backsheet 40 is a single layer polyethylene film. Such a preferred polyethylene film is available from Daedong Co. Ltd., KyungBuk-Do, Korea, under Code No. DNF-040712VL.

The backsheet 40 preferably has a microporous structure which can permit vapors to escape from the absorbent core 42 (often called "breathable backsheet") while still preventing body fluids from passing through the backsheet 40. A preferred microporous polyethylene film is available from Mitsubishi Chemical Corporation, Tokyo, Japan, under Code No. NPP2. The backsheet 40 can be embossed to provide a cloth-like appearance.

The absorbent core 42 is capable of receiving, absorbing or retaining body fluids discharged. The absorbent core 42 is preferably compressible, conformable, and non-irritating to the wearer's skin. The absorbent core 42 can be formed by a single layer material or a plurality of layers of materials. The absorbent core may include any of a wide variety of liquid-absorbent materials commonly used in absorbent articles, such as comminuted wood pulp, which is generally referred to as airfelt. A particularly preferred absorbent core material is an airfelt material which is available from Weyerhaeuser Company, Washington, USA, under Code No. NB416.

Examples of other suitable absorbent materials for use in the absorbent core include creped cellulose wadding; melt-blown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; absorbent gelling materials; or any equivalent material or combinations of materials, or mixtures of these.

The absorbent core 42 may be manufactured in a wide variety of sizes and shapes. The periphery of the absorbent core 42 thus can take any shape in its top plane view. Preferred shapes for the core periphery include an oval, a rectangle, an hourglass, and a combination of the oval and rectangle such as the one shown in FIG. 1.

In a preferred embodiment for a relatively thick, overnight, extra protection sanitary napkin, the sanitary napkin 20 has a total core length ranging between about 200 and 450 mm. A length shorter than about 200 mm typically does not extend far enough into the gluteal area to provide improved protection. A length longer than about 400 mm generally extends too far beyond the gluteal groove for all of the rear end region to conform to the wearer's buttocks leading to poor gluteal fit.

Figure 4:
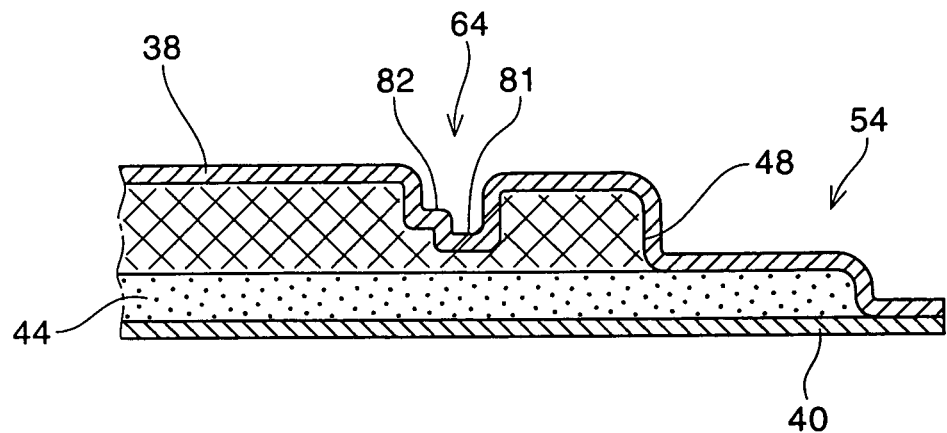
FIG. 4 is a schematic cross-sectional view of the absorbent article shown in FIG. 1 taken along line 4-4 of FIG. 1.

FIG. 4 is a schematic cross-sectional view of the sanitary napkin 20 shown in FIG. 1 taken along line 4-4 of FIG. 1. The rear side flaps 54 extend laterally outward from the corresponding longitudinal edge 48 of the absorbent core 42 in the rear end region 30. Preferably, the sanitary napkin 20 further includes a continuous support layer 44 which is disposed between the absorbent core 42 and the backsheet 40 in (at least a part of) the rear end region 30 (and the front region 28 and the central region 32 if desired). The continuous support layer 44 extends laterally into the rear side flaps 54 in the rear end region 30. Herein, "continuous layer" means a layer (or member) that does not include two (or more) component materials physically separated (or spaced apart) within the layer. For example, if a layer (or member) includes two component materials which are not directly bonded or connected one another, that layer is not a continuous layer but a discontinuous layer. The continuous support layer 44 should have sufficient thickness, rigidity and resiliency to prevent the rear side flaps 54 from bunching (i.e., deforming or twisting) which tends to be cased by a stress generated between the rear side flaps 54 and the undergarment during use.

The continuous support layer 44 can be formed by a wide variety of materials (preferably hydrophilic), preferably fibrous materials. Preferred fibrous materials include nonwoven materials. The fibers or other components of such nonwoven materials may be synthetic or natural, or partially synthetic and partially natural. Suitable synthetic fibers include polyester, polypropylene, polyethylene, nylon, viscous rayon, or cellulose acetate fibers. Suitable natural fibers include cotton, cellulose, or other natural fibers.

In one preferred embodiment, the continuous support layer 44 is an air laid nonwoven material which is available from Kang Na Hsiung Enterprise Co., Ltd., Taipei, Taiwan, under Code No. AL080-BL01-10. This nonwoven material has basis weight of 80 g/m$^2$, density of 0.07 g/cm$^3$, and thickness of 1.16 mm. This nonwoven material is formed by a mixture of chemical pulp (or cellulose) fibers and polyethylene/polypropylene bi-component fibers through an air through process. In order to provide the desired support effect for the rear side flaps 54 under in-use conditions, it is desirable that the nonwoven material for the continuous support layer 44 preferably has basis weight of 30~180 g/m$^2$, density of 0.05~0.20 g/cm$^3$, and thickness of 0.3~1.5 mm.

Referring again to FIG. 4, the sanitary napkin 20 preferably includes an adhesive layer (not shown in FIGs.) disposed between the continuous support layer 44 and the backsheet 40 in the rear end region 30. Preferably, the adhesive layer is applied uniformly between the continuous support layer 44 and the backsheet 40. Thus, the uniform adhesive layer uniformly bonds the continuous support layer 44 to the backsheet 40 in the rear end region 30. The uniform adhesive layer is preferred since it can help provide a uniform thickness, rigidity and/or resiliency to the rear side flaps 54 which can also prevent the rear side flaps 54 from bunching which may be cased by a stress generated between the rear side flaps 54 and the undergarment during use.

The topsheet 38, the backsheet 40, the absorbent core 42 may be assembled in a variety of configurations known in the art. Preferred configurations are described in U.S. Pat. Nos. 4,950,264; 5,009,653 issued to Osborn; U.S. Pat. No. 4,425,130 issued to DesMarais; U.S. Pat. Nos. 4,589,876 and 4,687,478 issued to Van Tilburg, and U.S. Pat. No. 5,234,422 issued to Sneller, et al.

Referring again to FIG. 1, the sanitary napkin 20 has a pair of outwardly convex longitudinal central channels 62 formed at least in the central region 32. Herein, "channel" refers to a generally elongated depression formed in at least a portion of an absorbent article. The channel can be formed by, for example, reducing the amount of the absorbent core at the channel portion, and/or compressing or embossing the absorbent core at the channel portion.

Typically, the channel is formed by applying a compressive force to both the topsheet and the absorbent core toward the backsheet. The topsheet at the channel portion is pushed down into the absorbent core, and the materials of the topsheet and the absorbent core are compressed at and below the bottom of the channel portion. By this operation (which is often called "embossing process"), the channel portion of the absorbent article has relatively higher density than the other portion(s) or the surrounding portion(s) of the channel portion. The channels of the present invention can be formed by any structures and processes known in the art.

The channel tends to preferentially diffuse or lead body fluids flow along the direction in which the channel extends. Therefore, the channel is useful to control body fluids flow within the absorbent article thereby preventing body fluids leakage from the absorbent article. The channel also tends to work as a preferential bending axis of the absorbent article. Therefore, the absorbent article may bend at the channel portion such that it provides an improved fit of the absorbent article to the wearer's body. It should be noted that such an improved fit of the absorbent article can also contributes an improvement in preventing body fluids leakage from the absorbent article.

The channel of the present invention can be either continuous or discontinuous. Herein, "discontinuous" means the channel can be separated by a non-channel portion (i.e., a portion where no channel is formed) such that the channel includes 2 or more elongated channel portions which are separated by a non-channel portion. The distance between the two succeeding channel portions (i.e., the length of the no channel portion) may be changed depending on the product design. Preferably, the length of the no channel portion is 0-20 mm, more preferably 2-10 mm, and yet more preferably 3-6 mm.

In one preferred embodiment, channels are formed by applying a uniform (or a single level of) compressive force to the topsheet and the absorbent core toward the backsheet. Alternatively, channels can be formed by applying two or more levels of compressive forces to the topsheet and the absorbent core toward the backsheet thereby forming a "two (or more) stage channel structure".

In the preferred embodiment shown in FIG. 1, the channels 62, 64, 65 and 66 are formed by applying two levels of compressive forces to the topsheet 38 and the absorbent core 42 toward the backsheet 40. The application of the two levels of compressive forces (i.e., higher compression and lower compression) produces two stage depth portions (i.e., "two stage channel structure") in the resulting the channels, i.e., first portion and second portion.

Figure 5:
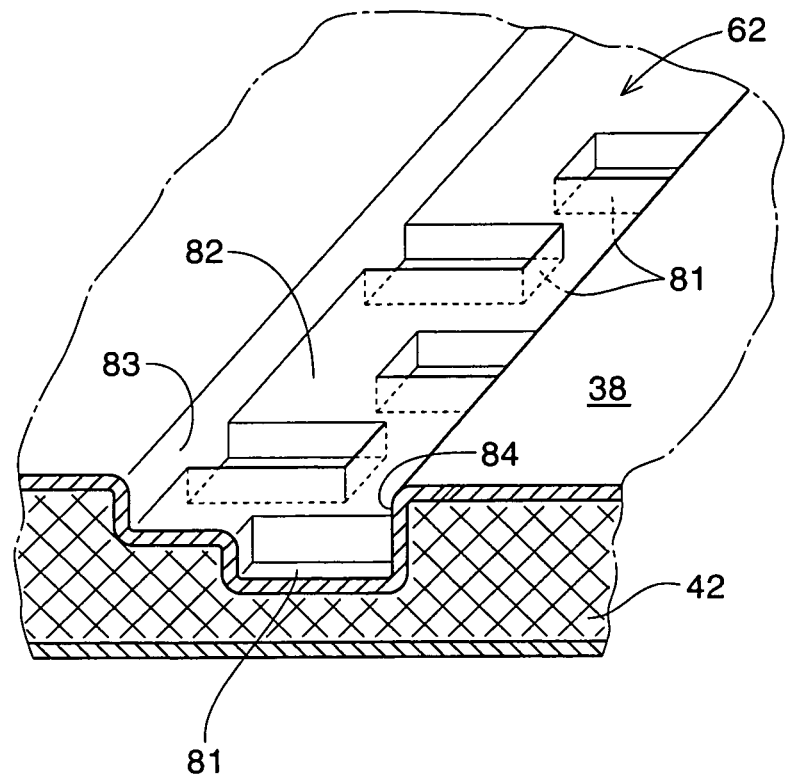
FIG. 5 is a perspective view of an emboss channel formed in the absorbent article shown in FIG. 1.

FIG. 5 is a perspective view of one channel formed in the sanitary napkin 20 shown in FIG. 1. In this embodiment, the channel 62 has two side walls (or channel walls) 83 and 84. The first portions 81 are formed by a higher compression, while the second portion 82 is formed by a lower compression. The absorbent core 42 is more compressed at the portions 81 of higher compression than the portion 82 of lower compression. In the embodiment shown in FIG. 5 (and also FIG. 3), the portions 81 of higher compression form the lowest portions of the channel 62, while the portion 82 of lower compression forms the higher portion in the channel 62. The first portions 81 of higher compression have a higher density than the portion 82 of lower compression as a result of compression force differences. Such a two stage channel structure is preferred since it can provide a better comfort to the wearer's body in use compared with the channel structure which has no stage difference (formed by no compression force differences applied). In addition, since the compression force is more concentrated at the portions 81 of higher compression, the two stage channel structure can also increase the bonding strength between the topsheet 38 and the absorbent core 42 at the portions 81.

The first portions 81 formed by a higher compression extend from one channel wall 83 but does not reach the other channel wall 84. In the embodiment shown in FIG. 5, the shape of the first portions 81 formed by a higher compression is about a rectangular. However, the shape of the first portions 81 can vary depending on the channel design in the sanitary napkin 20. The length, width and depth of the first portions 81 can also vary depending on the channel design in the sanitary napkin 20. Similarly, the shape, the length, width and depth of the second portion 82 can also vary depending on the channel design in the sanitary napkin 20.

The first portions 81 formed by a higher compression are spaced one another. The distance or interval of two adjacent portions 81 can be either consistent or inconsistent. In the embodiment shown in FIG. 5, the distance of two adjacent portions 81 is consistent.

In an alternative embodiment (not shown in FIGs.), the first portions 81 may be formed by lower compression, and the second portion 82 may be formed by higher compression. This produces an opposite geographic shape of the channels.

A variety of preferred channel structures which are applicable to the present invention are disclosed in, for example, U.S. Pat. No. 6,563,013 issued to Murota on May 13, 2003. This publication discloses examples of "two stage channel structure" which are preferably applicable to the embodiments of the present invention.

In the embodiment shown in FIG. 5, the first portion 81 formed by a higher compression extends from one channel wall 83 but does not reach the other channel wall 84. This channel structure is referred to as a "stitched channel structure".

However, this is not always necessary. Alternatively to such a stitched channel structure, the first portion 81 formed by a higher compression can extend from one channel wall 83 to the other channel wall 84. Such a structure can be produced by an application of higher and lower compressions alternatively applied along the longitudinal direction of the channel 62. Such channel structures are disclosed in, for example, U.S. Pat. No. 5,795,345 issued to Mizutani et al. on Aug. 18, 1998.

Figure 6:
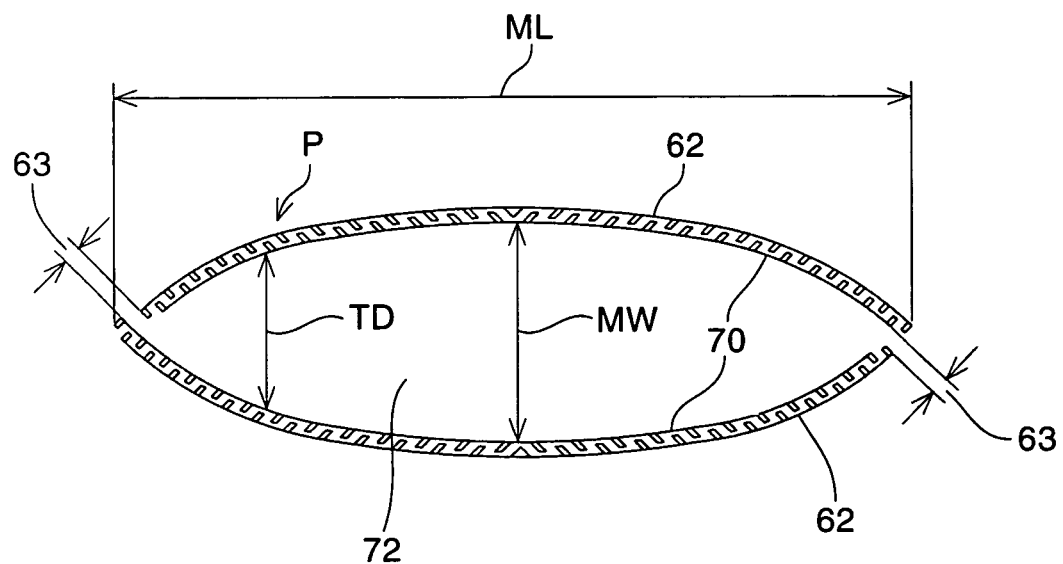
FIG. 6 is a plane view of the pair of outwardly convex longitudinal channels shown in FIG. 1.

FIG. 6 is a plane view of the pair of outwardly convex longitudinal central channels 62 shown in FIG. 1. Herein, "outwardly convex" means the longitudinal channels have a curved line shape (including a polygonal lines shape and a curved line shape) which is outwardly extended when looking from the longitudinal centerline L. The longitudinal central channels 62 shown in FIG. 1 have a circular arc shape which is outwardly curved when looking from the longitudinal centerline L of the sanitary napkin 20. The traversal distance TD of the pair of outwardly convex longitudinal central channels 62 decreases towards the both ends of the central channels 62 to define a central closed area 72.

Herein, "closed area" is an area that is disposed between the inside channel wall(s) of the outwardly convex longitudinal channels. When the traversal distance between the inside channel walls of the outwardly convex longitudinal channels reaches 60% of the maximum traversal distance, a closed area is defined at least at that position. However, the closed area can extend within the inside channel walls of the outwardly convex longitudinal channels until they stop at their ends (before they intersect).

In one preferred embodiment, the closed area is defined at least at the position where the traversal distance between the inside channel walls of the outwardly convex longitudinal channels reaches 20% (or less than 5% or about 0% if desired) of the maximum traversal distance. Thus, it should be noted that the "closed area" does not require an area that is physically "closed" by the outwardly convex longitudinal channels. The closed area has a maximum length (ML) and a maximum width (MW). The maximum length is defined as the longitudinal distance between the outermost walls at the both ends of the outwardly convex longitudinal channels. The maximum width is defined as the maximum traversal distance between the inside channel walls of the outwardly convex longitudinal channels. (These maximum length and width ML and MW of the closed area are shown in FIG. 6.)

In the embodiment shown in FIG. 6, the central closed area 72 is defined at least at the position P where the traversal distance TD between the outwardly convex longitudinal central channels 62 reaches 60% of the maximum traversal distance. However, the closed area 72 extends within the inside channel walls of the outwardly convex longitudinal channels 62 until they stop at their ends.

The closed area preferably has a periphery wherein 70-100% in length of the periphery is surrounded by the outwardly convex longitudinal channels. In other words, the rest (i.e., 0-30% in length) of the periphery may be surrounded by other channel(s). Preferably, 80-98% in length of the periphery of the closed area is defined by the outwardly convex longitudinal channels.

The closed area generally tries to maintain the body fluids absorbed underneath the closed area (e.g., an absorbent core). In addition, the closed area also works to prevent the material of the absorbent core from moving when it becomes wet by the absorbed body fluids.

The central closed area 72 shown in FIG. 6 has a periphery 70 defined by the inside channel walls of the two central channels 62. Preferably, 70-100% in length of the periphery 70 is surrounded by the outwardly convex longitudinal channels 62. In the embodiment shown in FIG. 6, since there is about 2% in length of the periphery 70 of the closed area having no channel portion 63, about 98% in length of the periphery 70 of the closed area 72 is defined by the outwardly convex longitudinal channels 62.

The pair of outwardly convex longitudinal central channels 62 can take any shape that defines a central closed area 72. Preferably, the central channels 62 takes an oval like shape. Preferred oval like shapes include, for example, an actual oval shape defined by mathematics and an eye shape (i.e., a shape formed by two arc like lines), and the like. In the preferred embodiment shown in FIG. 1, the central channels 62 has an eye shape consisting of two arc like lines, each of which is formed by five (5) circular arcs which are connected in series. Such oval like shapes have a maximum length ML and a maximum width MW. The central closed area 72 shown in FIG. 6 has a maximum length ML and a maximum width MW.

Preferably, the central closed area 72 has a maximum length ML of 80-220 mm and a maximum width MW of 25-70 mm. More preferably, the central closed area 72 has a maximum length ML of 130-190 mm and a maximum width MW of 35-55 mm. In the preferred embodiment shown in FIG. 1, the central closed area 72 has a maximum length ML of 160 mm and a maximum width MW of 46 mm.

Referring again to FIG. 1, the sanitary napkin 20 preferably has a rear channel 64 defining a rear closed area 74 in the rear end region 30. The rear closed area 74 can be formed not only within the rear end region 30 but both or either the central region 32 and/or the rear end region 30. For example, in the embodiment shown in FIG. 1, the rear closed area 74 is formed within the rear end region 30. On the other hand, in the embodiment shown in FIG. 9 (which is discussed in later), the rear closed area 74 is formed within both the central region 32 and the rear end region 30.

Preferably, the maximum width of the rear closed area 74 is no greater than that of the maximum width of the central closed area 72. By limiting the width of the rear closed area 74 within the maximum width of the central closed area 72, the discharged body fluids are led along the longitudinal direction more than the traversal direction by the fluids control function of the rear channels 64. Therefore, this configuration is useful to prevent the body fluids leakage from the longitudinal edges 22 of the sanitary napkin 20 in the rear end region 30. In preferred embodiment shown in FIG. 1, the maximum width of the rear closed area 74 is about same as that of the maximum width of the central closed area 72.

The rear channel 64 can take any shape that forms a closed area. The rear channel 64 preferably takes an oval like shape or an elongated U-character shape. Preferred oval like shapes include, for example, an actual oval shape defined by mathematics and an elongated U-character shape. A preferred elongated U-character shape has the traversal distance between the two arms of the elongated U-character shape decreases towards the central closed area 72 as shown in FIG. 1.

In a preferred embodiment, the sanitary napkin 20 further has an additional (or secondary) rear channel 65 within the rear closed area 74 in the rear end region 30 as shown in FIG. 1. The additional rear channel 65 does not need to form a closed area. The additional rear channel 65 is used to control the rigidity of the sanitary napkin 20 at the rear end region 30. In addition, the additional rear channel 65 also can work to maintain the absorbed body fluids in the inside area of the channel 65. The additional rear channel 65 can take any shape but it preferably takes an elongated U-character shape as shown in FIG. 1.

Referring again to FIG. 1, the sanitary napkin 20 preferably has a front channel 66 forming a front closed area 76 in the front end region 30.

The front closed area 76 can be formed not only within the front end region 28 but both the central region 32 and the front end region 28. For example, in the embodiment shown in FIG. 1, the front closed area 76 is formed within the front end region 30. On the other hand, in the embodiment shown in FIG. 9 (which is discussed in later), the front closed area 76 is formed within both the central region 32 and the front end region 30.

Preferably, the maximum width of the front closed area 76 is no greater than that of the maximum width of the central closed area 72. By limiting the width of the front closed area 76 within the maximum width of the central closed area 72, the discharged body fluids are led along the longitudinal direction more than the traversal direction by the fluids control function of the front channels 66. Therefore, this configuration is also useful to prevent the body fluids leakage from the longitudinal edges 22 of the sanitary napkin 20 in the front end region 28. In preferred embodiment shown in FIG. 1, the maximum width of the front closed area 76 is about same as that of the maximum width of the central closed area 72.

The front channel 66 can also take any shape that forms a closed area. The front channel 66 preferably takes a horseshoe like shape, an oval or circle like shape or a U-character shape. One example of preferred horseshoe like shape is shown in FIG. 1.

In one embodiment, the absorbent core 42 is non-profiled within the central closed area 72 so that the central region 32 has the same caliper as the outside of the central closed area 72. Preferably, the absorbent core 42 is profiled within the central closed area 72 so that the central region 32 has a caliper that is greater than the caliper of the outside of the central closed area 72 (i.e., a non-profiled portion) as shown in FIGS. 2 and 3. Herein, "profiled" means that one specified portion of a material has a caliper that is greater than that of the other portion to be compared. Herein, calipers are measured under a pressure of 0.5 psi using a circular comparator foot with a 1 inch diameter area. Typically, a profiled portion is formed by increasing the amount of material(s) at the profiled portion of the absorbent core than the other adjacent portion such that the profiled portion shows an expanded shape (or appearance) on the body surface 20A compared to the other portion. In the embodiment of FIG. 1, the absorbent core 42 contains an increased amount of material(s) within the central closed area 72 than the outside of the central closed area 72 such that the sanitary napkin 20 is profiled at the central closed area 72 as shown in FIG. 2.

Preferably, the front end region 28 and the rear end region 30 have the same or similar caliper, while the central region 32 comprises the greatest caliper portion of the sanitary napkin 20 as a result of the profiled structure. The caliper ratio of the profiled portion to the non-profiled portion preferably ranges from about 1.1:1 to about 3:1, and more preferably from about 2:1 to about 2.6:1. In the sanitary napkin 20 shown in FIG. 1, the caliper ratio of the profiled portion to the non-profiled portion is about 2.2:1.

The sanitary napkin 20 can be of any caliper, including relatively thick, relatively thin, or even very thin. The embodiment of the sanitary napkin 20 shown in FIG. 1 is intended to be an example of a relatively thick, overnight, extra protection sanitary napkin having a caliper of about 5 mm in the end regions 28 and 30 and a caliper of about 14 mm in the central region 32. It should be understood, however, when viewing these figures the number of layers of material shown may cause the sanitary napkin 20 to appear much thicker than it actually is, particularly in cross-section.

As shown in FIG. 1, the sanitary napkin 20 is asymmetrically shaped so that the rear end region 30 is larger than the front end region 28. In the preferred embodiment shown in FIG. 1, the sanitary napkin 20 is asymmetrically shaped such that the rear end region 30 has both a larger width and a longer length than the front end region 28. The widths of the front and rear end regions are defined by the traversal distance between the longitudinal edges 22 of the sanitary napkin 20. The ratio of the widths of the rear end region 30 to the front end region 28 preferably ranges from between about 1:1 and about 2.5:1. More preferably, the ratio of the widths of the rear end region 30 to the front end region 28 is about 1.4:1. The ratio of the longitudinal lengths of the front end region 28 to the central region 32 is from about 1:1 to about 1:4, and the ratio of the longitudinal lengths of the central region 32 to the rear end region 30 is from about 1:0.5 to about 1:3. In the preferred embodiment shown in FIG. 1, the ratio of the longitudinal lengths of the front end region 28 to the central region 32 and the rear end region 30 is about 1:1.7:2.5.

The topsheet 38 and the backsheet 40 typically have length and width dimensions generally larger than those of the absorbent core 42. The topsheet 38 and backsheet 40 extend beyond the edges of the absorbent core 42, and are joined together to form a pair of central side flaps 52 and a pair of rear side flaps 54. These topsheet 38 and backsheet 40 can be joined any means (e.g., an adhesive) known in the art.

The central side flaps 52 can be in any suitable configuration and shape known in the art. Suitable flaps are described in U.S. Pat. No. 5,389,094 issued to Lavash, et al. on Feb. 14, 1995; and U.S. Pat. No. 5,558,663 issued to Weinberger, et al. on Sep. 24, 1996.

In the embodiment shown in FIG. 1, the central side flaps 52 and the rear side flaps 54 are integral with the main body portion 25 of the sanitary napkin 20 (i.e., these flaps comprise integral extensions of the topsheet 38 and the backsheet 40 from the main body portion 25). Alternatively, these flaps can be formed by separate materials from the topsheet 38 and the backsheet 40, which are joined to the main body portion 25 of the sanitary napkin 20 in any suitable manner. In that event, the flaps are each joined to (or associated with) the main body portion 25 along a juncture, typically a longitudinally-oriented (or "longitudinal") juncture (not shown in Figs.).

The central side flaps 52 and the rear side flaps 54 are used to attach the sanitary napkin 20 to the wearer's panties or undergarment through adhesive fasteners as known in the art. The fasteners comprise a plurality of patches of adhesive adhered to the garment surface 20B of the backsheet 40 of the sanitary napkin 20.

Figure 7:
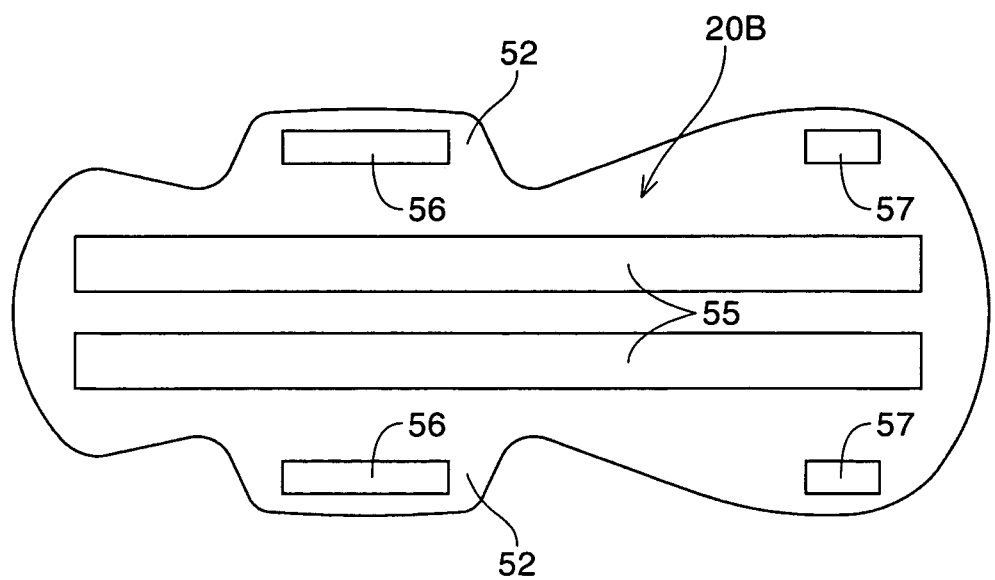
FIG. 7 is a bottom plane view of the absorbent article shown in FIG. 1.

FIG. 7 is a bottom plane view of the sanitary napkin 20 shown in FIG. 1. Typically one or two (or more if desired) adhesive patches (i.e., panty fastening adhesive 55) are disposed on the main body portion 25 of the sanitary napkin 20 such that the sanitary napkin 20 can adhere to the crotch area of the wearer's undergarment to keep the sanitary napkin 20 in place.

The panty fastening adhesive 55 is preferably at least about 50% as long as the absorbent core 42, but is preferably no greater than about 100% of the length of the core 42. The preferred length of the panty fastening adhesive 55 is between about 75% and about 90% the length of the absorbent core 42. The width of the panty fastening adhesive 55 is preferably at least about 25% of the width of the portion of the absorbent core 42 lying in the front end region 28, but should be no wider than about 100% the width of the portion of the core 42 in the front end region 28. The preferred width of the panty fastening adhesive 55 is between about 70% and about 88% of the width of the first end region core width.

In addition, a pair of additional adhesive patches (i.e., central flap adhesives 56) are disposed on the garment surface 20B of the central side flaps 52 of the sanitary napkin 20 to adhere to the undersides of the wearer's undergarment during use and to keep the napkin 20 in place to improve fit.

Preferably, another pair of additional adhesive patches (i.e., rear flap adhesives 57) are disposed on the garment surface 20B of the rear side flaps 54 of the sanitary napkin 20 to additionally help keep the sanitary napkin 20 in place. The rear flap adhesives 57 adheres to the undersides of the wearer's undergarment during use and to keep the napkin 20 in place to improve fit. The rear flap adhesives 57 jointly work with the continuous support layer 44 in the rear side flaps 54 to prevent the rear side flaps 54 from undesirable bunching during the use of the sanitary napkin 20.

The central side flaps 52, which have panty fasteners thereon, adhere to the underside of the wearer's undergarment. The central side flaps 52 serve to keep the sanitary napkin 20 in place during wear. Keeping the sanitary napkin 20 in place prevents skewing of the napkin 20 in the panty, and undesirable bunching. The central side flaps 52 may also assist the central region 32 in forming into the desired W-shaped configuration, and the rear end region 30 in forming the desired inverted V-shaped configuration.

These adhesive patches are preferably covered by release strips before use as known in the art. Preferably, the central side flaps 52 are folded over the topsheet 38 and they are bridged by a single (or unitary) release strip through the central flap adhesives 56. Similarly, the rear side flaps 54 are also folded over the topsheet and they are also bridged by a single (or unitary) release strip through the rear flap adhesives 57. In a particularly preferred embodiment, both the central side flaps 52 and the rear side flaps 54 are bridged by a single (or unitary) release strip. Herein, "unitary" means the release strip member can be formed by either a single material or two (or more) joined materials.

The panty fastening adhesive 55 is also covered by a release strip. If desired, the panty fastening adhesive 55 is covered by a releasable wrapper that also serves as an individual wrapper package for the sanitary napkin 20. A preferred structure is described in U.S. Pat. No. 6,074,376 issued to Mills on Jun. 13, 2000.

The sanitary napkin 20 is worn by the wearer so that the rear end region 30 is placed to the rear of the wearer's body to provide the best gluteal fit. The outwardly convex longitudinal central channels 62 assist the central region 32 of the sanitary napkin 20 in assuming a W-shaped cross-sectional configuration when the napkin 20 is laterally compressed by the wearer's thighs, thereby allowing improved contact with the wearer's genital area. This W-shaped configuration is formed by the sides compressing upwards and inwards and the center buckling upward into a convex upward configuration, with the densified region provided by the channels forming the fold lines.

In addition, due to the profiled configuration in the central region 32, the central closed area 72 is brought more closely to the source area of body fluids thereby contributing to a further better fit to the wearer's body. The profiled configuration of the central closed area 72 cooperates with the W-shaped cross-sectional configuration thereby allowing the central closed area 72 to closely fit to the wearer's genital area. This cooperative function enables an improved leakage protection at the central region 32.

The W-shape configuration of the central region 32 is transformed into an inverted V-shape configuration in the rear end region 30. The inverted V-shape configuration retains the profiled central portion of the W-shape configuration to improve gluteal fit. The rear end region 30 is thus also able to closely fit into the crevice between the wearer's buttocks (that is, in the gluteal groove) for improved protection from end soiling. This occurs while the rear end region 30 maintains its area coverage due to the size of the same and the panty fastening adhesive.

As a result, in the embodiment shown in FIG. 1, all the asymmetrical shape of the sanitary napkin 20, the embossed channels 62, 64 and 66, the central and rear side flaps 52 and 54, and the profiled configuration in the central closed area 72 cooperatively work together thereby providing an improved fit and leakage protection.

Figure 8:
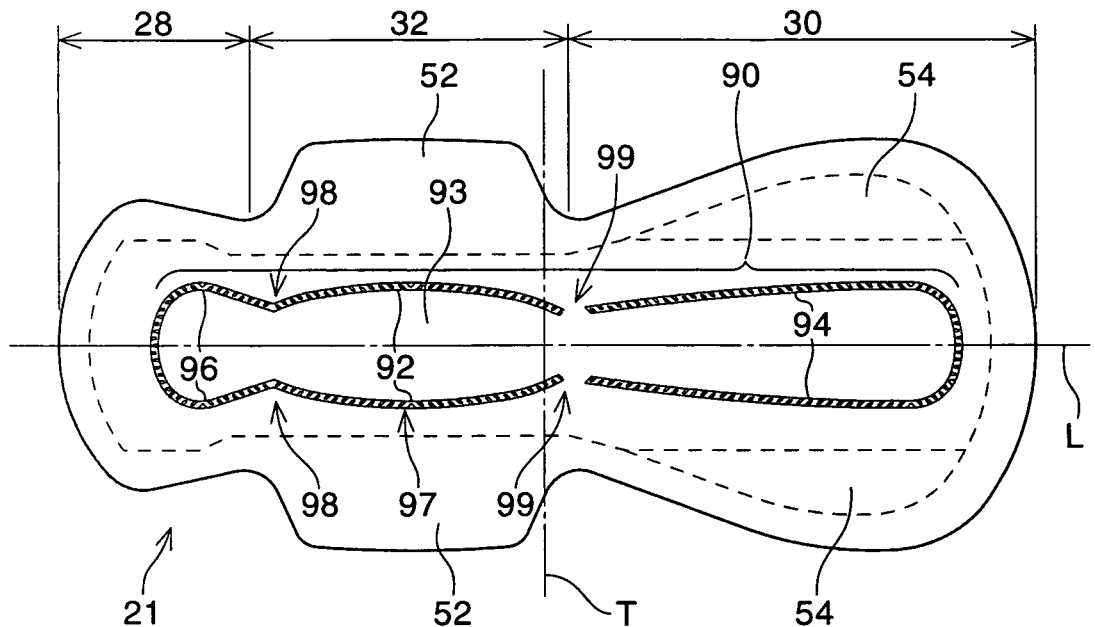
FIG. 8 is a top plane view of another preferred embodiment of the absorbent article of the present invention.

FIG. 8 is a top plane view of another preferred embodiment of the absorbent article of the present invention. In this embodiment, the absorbent article is also a relatively thick, overnight, extra protection, disposable sanitary napkin 21. It should be noted that except the channels arrangements the sanitary napkin 21 is similar to the sanitary napkin 20 which is discussed hereinabove. Referring to FIG. 8, the sanitary napkin 21 has a pair of longitudinal channels 90 formed in the front end region 28, the central region 32 and the rear end region 30; and a pair of central side flaps 52 each extending laterally outward from the central region 32. Each of the longitudinal channel 90 includes (or divided into) an outwardly convex central channel 92, an outwardly convex rear channel 94 and an outwardly convex front channel 96. The longitudinal channel 90 has (1) an outwardly convex channel portion 97 in the central region, (2) a front inwardly concave channel portion 98 at the transition area between the front end region 28 and the central region 32, and (3) a rear inwardly concave channel portion 99 at the transition area between the rear end region 30 and the central region 32.

Herein, "inwardly concave" means the longitudinal channels have a curved line shape (including a polygonal lines shape and a curved line shape) which is inwardly curved when looking from the longitudinal centerline L. The longitudinal channels 90 shown in FIG. 8 have a circular arc shape which is inwardly concave at the portions 98 and 99 when looking from the longitudinal centerline L of the sanitary napkin 20.

In one embodiment, the absorbent core 42 can be non-profiled within the central closed area 72. However, similarly to the sanitary napkin 20 shown in FIG. 1, the absorbent core 42 of the sanitary napkin 21 is preferably profiled in the central area 93 between the front inwardly concave channel portion 98 and the rear inwardly concave channel portion 99 so that the central region 32 has a caliper that is greater than the caliper of the outside of the central area 93 (i.e., a non-profiled portion).

Due to the profiled configuration in the central region 32, the central area 93 is brought more closely to the source area of body fluids thereby contributing to a further better fit to the wearer's body. The profiled configuration of the central area 93 cooperates with the W-shaped cross-sectional configuration formed by the outwardly convex central channels 92 thereby allowing the central area 93 to closely fit to the wearer's genital area. This cooperative function enables an improved leakage protection at the central region 32.

Figure 9:
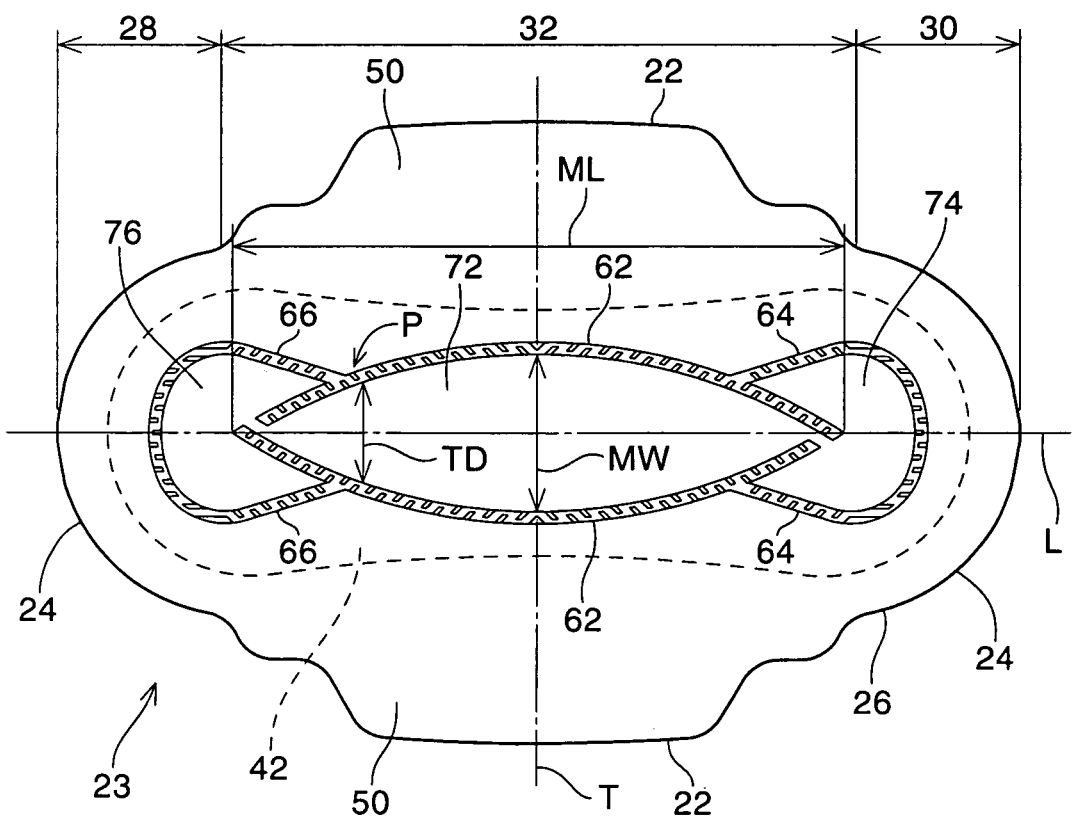
FIG. 9 is a top plane view of yet another preferred embodiment of the absorbent article of the present invention.

FIG. 9 is a top plane view of yet another preferred embodiment of the absorbent article of the present invention. In this preferred embodiment, the absorbent article is a thick disposable sanitary napkin 23 which is designed for a user who tends to have heavy discharge of body fluids in daytime. It should be noted, however, that this sanitary napkin 23 is relatively thinner and smaller compared with the sanitary napkin 20 shown in FIG. 1.

Referring to FIG. 9, the sanitary napkin 23 has two centerlines, a longitudinal centerline L and a transverse centerline T. The sanitary napkin 23 has two spaced apart longitudinal edges 22 and two spaced apart transverse or end edges (or "ends") 24, which together form the periphery 26 of the sanitary napkin 23. The sanitary napkin 23 also has two end regions, i.e., a front end region 28 and a rear end region 30. A central region 32 is disposed between the end regions 28 and 30. The sanitary napkin 23 includes a pair of side flaps 50 in the central region 32. Similarly to the central side flaps 52 in FIG. 1, the side flaps 50 can be also in any suitable configuration or shape known in the art.

As shown in FIG. 9, the sanitary napkin 23 is symmetrically shaped so that the shapes, areas, lengths and widths of the rear end region 30 and the front end region 28 are same. The ratio of the lengths of the end region 28 or 30 to the central region 32 can vary from about 1:5 to about 1:1, preferably from about 1:4 to about 1:3 In the sanitary napkin 23 shown in FIG. 9, this ratio is about 1:3.4.

Similarly to the sanitary napkin 20 shown in FIG. 1, the sanitary napkin 23 shown in FIG. 9 generally comprises a liquid pervious topsheet 38; a liquid impervious backsheet 40; an absorbent core 42 disposed between the topsheet 38 and the backsheet 40. The topsheet 38, backsheet 40, and absorbent core 42 can comprise any types of materials and structures known in the art as being suitable for such components of an absorbent article or a sanitary napkin.

The sanitary napkin 23 shown in FIG. 9 has a pair of outwardly convex longitudinal central channels 62 formed at least in the central region 32. The traversal distance TD of the pair of outwardly convex longitudinal central channels 62 decreases towards the both ends of the central channels 62 to define a central closed area 72. In the embodiment shown in FIG. 9, the central closed area 72 is defined at least at the position P where the traversal distance TD between the outwardly convex longitudinal central channels 62 reaches 60% of the maximum traversal distance TD. However, the closed area 72 extends within the inside channel walls of the outwardly convex longitudinal channels 62 until they stop at their ends.

Preferably, the central closed area 72 has a maximum length ML of 105-165 mm and a maximum width MW of 20-60 mm. More preferably, the central closed area 72 has a maximum length ML of 120-150 mm and a maximum width MW of 30-50 mm. In the preferred embodiment shown in FIG. 9, the central closed area 72 has a maximum length ML of 135 mm and a maximum width MW of 38 mm.

The sanitary napkin 23 preferably has a rear channel 64 defining a rear closed area 74 in the rear end region 30. The rear closed area 74 is formed within the central region 32 and the rear end region 30. The sanitary napkin 23 preferably has a front channel 66 forming a front closed area 76 in the front end region 30. The front closed area 76 is formed within the central region 32 and the front end region 28. The front and rear channels 66 and 64 can take any shape that form a closed area. The front and rear channels 66 and 64 preferably take a horseshoe like shape, an oval or circle like shape or a U-character shape. One example of preferred horseshoe like shape is shown in FIG. 9.

In one embodiment, the absorbent core 42 can be non-profiled within the central closed area 72. However, the absorbent core 42 is preferably profiled within the central closed area 72 so that the central region 32 has a caliper that is greater than the caliper of the outside of the central closed area 72 (i.e., a non-profiled portion). Preferably, the front end region 28 and the rear end region 30 have the same or similar caliper, while the central region 32 comprises the greatest caliper portion of the sanitary napkin 20 as a result of the profiled structure. The caliper ratio of the profiled portion to the non-profiled portion preferably ranges from about 1.1:1 to about 3:1, and more preferably is from about 2:1 to about 2.6:1. In the sanitary napkin 23 shown in FIG. 9, the caliper ratio of the profiled portion to the non-profiled portion is about 2.4:1.

In the embodiment shown in FIG. 9, the sanitary napkin 23 has a caliper of about 3.5 mm in the end regions 28 and 30 and a caliper of about 8.5 mm in the central region 32.

The sanitary napkin 23 is worn by the wearer so that the rear end region 30 is placed to the rear of the wearer's body. The outwardly convex longitudinal central channels 62 assist the central region 32 of the sanitary napkin 23 in assuming a W-shaped cross-sectional configuration when the napkin 23 is compressed by the wearer's thighs. This W-shaped configuration is formed by the sides compressing upwards and inwards and the center buckling upward into a convex upward configuration, with the densified region provided by the channels forming the fold lines.

In addition, due to the profiled configuration in the central region 32, the central closed area 72 is brought more closely to the source area of body fluids or the wearer's genital area thereby contributing to a further better fit to the wearer's body. The profiled configuration of the central closed area 72 cooperates with the W-shaped cross-sectional configuration thereby allowing the central closed area 72 to closely fit to the wearer's genital area. This cooperative function enables an improved leakage protection at the central region 32.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a pair of longitudinal edges, front and rear transverse edges, a front end region, a rear end region, and a central region disposed between the front and rear end regions, the absorbent article comprising:
a liquid pervious topsheet;
a liquid impervious backsheet;
an absorbent core disposed between the topsheet and the backsheet;
a pair of outwardly convex longitudinal central channels formed at least in the central region, the traversal distance between the pair of outwardly convex longitudinal central channels decreasing towards both ends of the channels to define a central closed area having a maximum width, wherein the traversal distance between the pair of outwardly convex longitudinal central channels reaches 20% of the maximum width;
a rear channel defining a rear closed area in the rear end region, the rear channel being discontinuous from the pair of outwardly convex longitudinal central channels; and
a continuous support layer disposed in the rear end region between the absorbent core and the backsheet, the continuous support layer being however absent in the central region;
the absorbent core being profiled within the central closed area so that the absorbent article in the central closed area has a caliper that is greater than a caliper of the absorbent article outside of the central closed area,
wherein the central region extends an entire width of the absorbent article between the pair of longitudinal edges, and the pair of longitudinal edges and front and rear transverse edges define a periphery of the absorbent article.

2. The absorbent article of claim 1 wherein a maximum width of the rear closed area is no greater than that of the maximum width of the central closed area.

3. The absorbent article of claim 2 further comprising a front channel defining a front closed area in the front end region, wherein a maximum width of the front closed area is no greater than that of the maximum width of the central closed area.

4. The absorbent article of claim 1 wherein the front end region has a width defined between the longitudinal edges, the rear end region has a width defined between the longitudinal edges, and the ratio of the width of the rear end region to the width of the front end region ranges between 1:1 and 2.5:1.

5. The absorbent article of claim 1 wherein the pair of outwardly convex central longitudinal channels assist the central region of the absorbent article in assuming a W-shaped cross-sectional configuration when the absorbent article is laterally compressed by a wearer's thighs, thereby allowing improved contact with a wearer's genital area.

6. The absorbent article of claim 1 further comprising a pair of central side flaps each extending laterally outward in the central region.

7. The absorbent article of claim 1 wherein the pair of outwardly convex longitudinal channels has higher compression portions and lower compression portions which are alternatively repeated along the longitudinal direction of the channel.

8. The absorbent article of claim 1 wherein the traversal distance between the pair of outwardly convex longitudinal central channels reaches 5% of the maximum width.

9. An absorbent article having a pair of longitudinal edges, front and rear transverse edges, a front end region, a rear end region, and a central region disposed between the front and rear end regions, the absorbent article comprising:
- a liquid pervious topsheet;
- a liquid impervious backsheet;
- an absorbent core disposed between the topsheet and the backsheet;
- a pair of outwardly convex longitudinal central channels formed at least in the central region, the traversal distance of the pair of outwardly convex longitudinal central channels decreasing towards the both ends of the channels to define a central closed area which has a maximum length of 80-220 mm and a maximum width of 25-70 mm;
- a rear channel defining a rear closed area in the rear end region; and
- a continuous support layer disposed in the rear end region between the absorbent core and the backsheet, the continuous support layer being however absent in the central region;
- the absorbent core being profiled within the central closed area so that the absorbent article in the central closed has a caliper that is greater than the caliper of the absorbent article outside of the central closed area,
- wherein the central region extends an entire width of the absorbent article between the pair of longitudinal edges, and the pair of longitudinal edges and front and rear transverse edges define a periphery of the absorbent article.

10. An absorbent article having a pair of longitudinal edges, front and rear transverse edges, a front end region, a rear end region, and a central region disposed between the front and rear end regions, the absorbent article comprising:
- a liquid pervious topsheet;
- a liquid impervious backsheet;
- an absorbent core disposed between the topsheet and the backsheet, the absorbent core being profiled within a central closed area so that the absorbent article in the central closed area has a caliper that is greater than the caliper of the absorbent article outside of the central closed area;
- a pair of central side flaps extending laterally outwardly from the central region; and
- a pair of rear side flaps extending laterally outwardly from the rear end region; and
- wherein the rear side flaps comprises a continuous support layer disposed between the absorbent core and the liquid impervious backsheet; and
- wherein the central region and the central side flaps do not contain the continuous support layer.

11. The absorbent article of claim 10 wherein the continuous support layer extends from one of the pair of rear side flaps to the other of the pair of rear side flaps.

* * * * *